United States Patent
Hu et al.

(10) Patent No.: US 12,146,817 B2
(45) Date of Patent: Nov. 19, 2024

(54) MICRO-ZONE SOIL SAMPLING APPARATUS AND METHOD FOR DIFFERENT CONTAMINATION SITUATIONS

(71) Applicant: Zhejiang University, Hangzhou (CN)

(72) Inventors: Baolan Hu, Hangzhou (CN); Meng Zhou, Hangzhou (CN); Wenda Chen, Hangzhou (CN); Jiaqi Wang, Hangzhou (CN)

(73) Assignee: Zhejiang University, Hangzhou (CN)

( * ) Notice: Subject to any disclaimer, the term of this patent is extended or adjusted under 35 U.S.C. 154(b) by 149 days.

(21) Appl. No.: 18/146,792

(22) Filed: Dec. 27, 2022

(65) Prior Publication Data

US 2023/0160786 A1     May 25, 2023

Related U.S. Application Data

(63) Continuation of application No. PCT/CN2020/122172, filed on Oct. 20, 2020.

(30) Foreign Application Priority Data

Jun. 28, 2020 (CN) .......................... 202010601576.9

(51) Int. Cl.
| | | |
|---|---|---|
| G01N 1/00 | (2006.01) | |
| G01N 1/08 | (2006.01) | |
| G01N 1/28 | (2006.01) | |
| G01N 33/24 | (2006.01) | |

(52) U.S. Cl.
CPC ............... *G01N 1/08* (2013.01); *G01N 33/24* (2013.01)

(58) Field of Classification Search
CPC .. G01N 1/00; G01N 1/08; G01N 1/28; G01N 33/24
See application file for complete search history.

(56) References Cited

FOREIGN PATENT DOCUMENTS

| | | | | |
|---|---|---|---|---|
| CN | 102087173 A | 6/2011 | | |
| CN | 104215747 A | 12/2014 | | |
| CN | 106124366 A | * 11/2016 | ............. | E21B 49/02 |
| CN | 108169102 A | * 6/2018 | ............. | G01N 15/08 |

(Continued)

OTHER PUBLICATIONS

Machine Translation of CN-108169102-A (Year: 2018).*
Machine Translation of CN-109187928-A (Year: 2019).*
Machine Translation of CN-211741269-U (Year: 2020).*

*Primary Examiner* — Nguyen Q. Ha

(57) ABSTRACT

A micro-zone soil sampling apparatus and method for different contamination situations. The apparatus includes an uncovered cylinder and a plurality of circular separators. The circular separators are vertically arranged in a hollow inner cavity of the uncovered cylinder, and are removably connected to an inner wall of the uncovered cylinder. Each circular separator includes a plurality of inner rings arranged coaxially, an outer ring coaxially arranged outside the inner rings, and a soil-bearing net. Each circular separator is divided into multiple hollow spaces by the inner rings and the outer ring. The inner rings made of a permeable membrane material and the outer ring made of a rigid material both have a certain thickness. The soil-bearing net is fittedly fixed on a bottom of each circular separator. A plurality of spokes passing through a center of the soil-bearing net are fixedly arranged on the soil-bearing net.

10 Claims, 2 Drawing Sheets

(56) References Cited

FOREIGN PATENT DOCUMENTS

| | | | | | |
|---|---|---|---|---|---|
| CN | 109187928 | A | * | 1/2019 | ............... G01N 1/28 |
| CN | 109270244 | A | * | 1/2019 | ............. G01N 33/24 |
| CN | 109975094 | A | | 7/2019 | |
| CN | 110296859 | A | | 10/2019 | |
| CN | 110940544 | A | | 3/2020 | |
| CN | 210604004 | U | | 5/2020 | |
| CN | 111751182 | A | | 10/2020 | |
| CN | 211741269 | U | * | 10/2020 | ............. G01N 33/24 |
| CN | 111999468 | A | * | 11/2020 | ............. G01N 33/24 |
| CN | 212621778 | U | | 2/2021 | |
| JP | 2005082998 | A | | 3/2005 | |
| WO | 2016196734 | A1 | | 12/2016 | |

* cited by examiner

MICRO-ZONE SOIL SAMPLING APPARATUS AND METHOD FOR DIFFERENT CONTAMINATION SITUATIONS

CROSS-REFERENCE TO RELATED APPLICATIONS

This application is a continuation of International Patent Application No. PCT/CN2020/122172, filed on Oct. 20, 2020, which claims the benefit of priority from Chinese Patent Application No. 202010601576.9, filed on Jun. 28, 2020. The content of the aforementioned application, including any intervening amendments thereto, is incorporated herein by reference in its entirety.

TECHNICAL FIELD

The disclosure relates to on-site contamination research, in particular to a micro-zone soil sampling apparatus and method for different contamination situations.

BACKGROUND

Soil, as a non-homogeneous porous medium, is a complex system constituted by various micro-zones under different physicochemical gradients and environmental conditions. Soil micro-zone refer to a zone that significantly differs in nature from the whole soil body and is significant for the soil productivity. The soil micro-zone can be divided into rhizosphere micro-zones and fertilizer micro-zones. For most parameters (e.g., soil pH, enzyme, nutrient and major elements), an influencing range of the rhizosphere micro-zone is 0.5-4 mm, while for gases, nitrates, water, and redox potential, the influencing range can exceed 4 mm. The fertilizer micro-zones are special environments around the fertilizers and fertilizer grains created by the input of inorganic or organic fertilizers into the soil. In these micro-zones, the fertilizer concentration is several or tens of times higher than that in the whole soil body, resulting in changes in the soil physicochemical properties and the soil microbial activity. Spatial studies based on the micro-zone level have shown that more than 80% of the soil bacteria inhabit the micro-porous spaces of the soil stable agglomerates since the micro-pores provide the most favorable water and nutrient conditions.

Due to the high heterogeneity of soils, some micro-zone environments are even more important than the whole. In the presence of inorganic or organic pollutants, a special environment will be formed around the pollutants, which leads to a steep pollutant concentration gradient that has a significant impact on the soil physicochemical properties and the microorganisms living in the micro-zones. However, less attention has been paid to the soil micro-zone structure of contaminated sites in the current researches, and there are few reports about the analysis of the soil physic-chemical properties, pollutant concentration, and microorganisms in the micro-zones under different pollution types and rainfall intensities. In addition, the existing simulators fail to simultaneously achieve the millimeter-scale simulation and sampling on the micro-zones along the vertical and horizontal directions.

SUMMARY

An object of this disclosure is to provide a micro-zone soil sampling device and method for different contamination situations to overcome the shortcomings and deficiencies of the prior art. By simulating different contamination modes (i.e., single contamination, combined contamination, low-concentration contamination, high-concentration contamination, intermittent contamination, and continuous contamination) and different rainfall levels (average rainfall and maximum rainfall), this application achieves the millimeter-scale micro-zone soil sampling along the vertical and horizontal directions under different contamination situations, such that the requirements of soil physicochemical index determination, pollutant concentration monitoring, and microbial phase analysis can be met. Therefore, this application is conducive to the investigation of the concentration gradient characteristics of pollutants in the micro-zone along the horizontal and vertical directions and analysis of the effects of pollutants on physicochemical properties and microorganisms in the micro-zone.

The technical solutions of the disclosure are described below.

In a first aspect, this application provides a micro-zone soil sampling apparatus, comprising:
    an uncovered cylinder; and
    a plurality of circular separators;
    wherein the plurality of circular separators are vertically arranged in a hollow inner cavity of the uncovered cylinder, and are removably connected to an inner wall of the uncovered cylinder; a connection between an outer circumference of each of the plurality of circular separators and an inner wall of the uncovered cylinder is sealed; and adjacent two circular separators are stacked;
    each of the plurality of circular separators comprises a plurality of inner rings, an outer ring, and a soil-bearing net; the plurality of inner rings are arranged coaxially; the outer ring is coaxially arranged outside the plurality of inner rings; the plurality of inner rings and the outer ring are arranged evenly spaced apart; each of the plurality of circular separators is divided into a plurality of circular hollow spaces by the plurality of inner rings and the outer ring; the plurality of inner rings and the outer ring both have a certain thickness; the plurality of inner rings are made of a permeable membrane material, and the outer ring is made of a rigid material; the soil-bearing net is fittedly fixed on a bottom of each of the plurality of circular separators, and is configured to bear a micro-zone soil sample; and a plurality of spokes passing through a center of the soil-bearing net are fixedly arranged on bottom of the soil-bearing net.

In some embodiments, each of the plurality of circular separators has a thickness of 1 mm, and comprises at least four inner rings.

In some embodiments, the soil-bearing net has a hole size of 5-15 m, and is made of nylon or stainless steel; and the plurality of spokes are made of a rigid material.

In some embodiments, a bottom of the uncovered cylinder is evenly provided with a plurality of through-holes having a diameter of 1-3 mm.

In a second aspect, this application provides a soil treatment method by using the micro-zone soil sampling apparatus, comprising:
    (S1) pre-treating a plurality of soil samples from different layers; spreading the plurality of soil samples evenly onto the plurality of circular separators, respectively; and successively placing the plurality of circular separators in the hollow inner cavity of the uncovered cylinder from a top of the uncovered cylinder, and fixing the plurality of circular separators on the inner wall of the uncovered cylinder;

(S2) adding an exogenous pollutant to an uppermost layer of the plurality of circular separators; and spraying simulated rain on the plurality of soil samples from the top of the uncovered cylinder;

(S3) successively removing the plurality of circular separators from the hollow inner cavity from top to bottom to achieve vertical differentiation of a millimeter-scale micro-zone of a contaminated site; after the plurality of circular separators are removed from the hollow inner cavity of the uncovered cylinder, scraping each of the plurality of soil samples from the hollow spaces of a corresponding circular separator successively, so as to achieve vertical differentiation of the millimeter-scale micro-zone of the contaminated site; and (S4) analyzing the plurality of soil samples.

In some embodiments, in step (S1), the plurality of soil samples are pre-treated by refining and drying.

In some embodiments, in step (S2), the exogenous pollutant is added at a center or an upper surface of the uppermost layer of the plurality of circular separators.

In some embodiments, in step (S2), the exogenous pollutant is a single pollutant or a compound pollutant, and is added according to different concentrations in an intermittent or continuous manner.

In some embodiments, in step (S2), an intensity of the simulated rain is determined according to an average rainfall per unit time or by simulating a rainfall intensity of a heavy rain according to a maximum rainfall.

In some embodiments, in step (S4), the plurality of soil samples are analyzed for physicochemical property, pollutant level, and microbial composition.

Compared to the prior art, the present disclosure at least has the following beneficial effects.

(1) The apparatus provided herein can be used in different contaminated site environments and achieve simulation of different contamination types (single contamination, combined contamination, low-concentration contamination, high-concentration contamination, intermittent contamination, and continuous contamination) and different rainfall levels (average rainfall and maximum rainfall).

(2) The apparatus provided herein adopts a circular structure in the horizontal direction and stacks a plurality of circular separators in the vertical direction, enabling simultaneous differentiation and sample collection of millimeter-level micro-zone soils in the horizontal and vertical directions under different pollution scenarios.

(3) The apparatus provided herein can meet the requirements of soil sample volume for determination of soil physicochemical determination, pollutant concentration monitoring, and microbial phase analysis at the millimeter scale, which aims to explore the characteristics of the horizontal and vertical concentration gradients of pollutants in the millimeter-scale micro-zone soil and analyze the effects of pollutants on soil physicochemical properties and microorganisms in the micro-zone soil.

Figure 1:
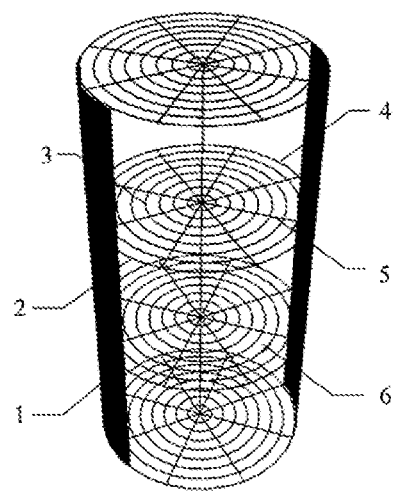
FIG. 1 is a structural diagram of a micro-zone soil sampling apparatus according to an embodiment of this disclosure.

In the drawings: 1, uncovered cylinder; 2, circular separator; 3, inner ring; 4 outer ring; 5, spoke; and 6, soil-bearing net.

DETAILED DESCRIPTION OF EMBODIMENTS

The present disclosure will be further described below with reference to the accompanying drawings and embodiments. The technical features of various embodiments of the present disclosure can be accordingly combined in the absence of contradictions.

Figure 2:
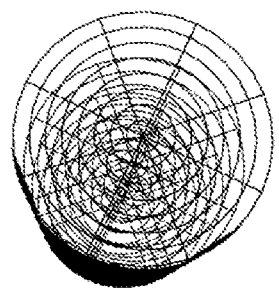
FIG. 2 is a top view of the micro-zone soil sampling apparatus according to an embodiment of this disclosure.

Referring to FIGS. 1-2, a micro-zone soil sampling apparatus is provided, which includes an uncovered cylinder 1, and a plurality of circular separators 2. The plurality of circular separators 2 are vertically arranged in a hollow inner cavity of the uncovered cylinder 1, and are removably connected to an inner wall of the uncovered cylinder 1. A connection between an outer circumference of each of the plurality of circular separators 2 and an inner wall of the uncovered cylinder 1 is sealed. An outer circumference of each of the plurality of circular separators 2 is detachably connected to the hollow inner cavity of the uncovered cylinder 1 for subsequent removal of the plurality of circular separators 2 from the hollow inner cavity of the uncovered cylinder 1. In the actual applications, the lowermost layer circular separator 2 can be arranged at the bottom of the uncovered cylinder 1, i.e., stackedly arranged on the bottom of the cylinder 1. In this case, the bottom of the uncovered cylinder 1 should be provided with a plurality of through holes having a diameter of 1-3 mm, which are evenly distributed on the bottom of the uncovered cylinder 1. The through holes provided herein are to simulate the loss of contaminants in the soil along a vertical direction and to prevent the accumulation of contaminants on the lowermost layer of the circular separator 2, which will affect the accuracy of the simulation.

Figure 3:
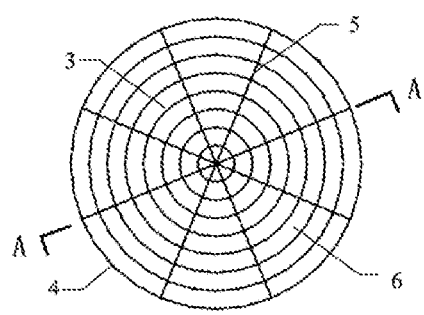
FIG. 3 is a structural diagram of a single circular separator of the micro-zone soil sampling apparatus according to an embodiment of this disclosure.
Figure 4:
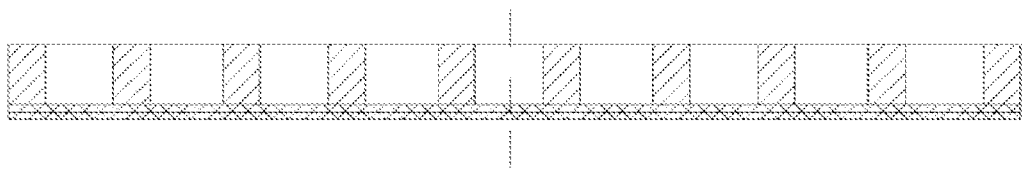
FIG. 4 is a sectional view of the circular separator in FIG. 3 along line A-A.

As shown in FIGS. 3-4, the circular separator 2 includes a plurality of inner rings 3, an outer ring 4, and a soil-bearing net 6. The circular separator 2 generally has a thickness of 1 mm to separate individual micro-zone soils. The number of the inner rings 3 can be multiple as needed, and is not less than four. The plurality of inner rings 3 are arranged coaxially, and the outer ring 4 is coaxially arranged on an outside of the plurality of inner rings. The distance between any adjacent two inner rings 3 is equal, and the distance between the adjacent two inner rings 3 is equal to the distance between the outermost inner ring 3 and the outer ring 4, that is, the distance between any adjacent two rings of the circular separator 2 is equal. In this case, the inner rings 3 and outer ring 4 divide the circular separator 2 into a plurality of annular hollow spaces. Both the inner rings 3 and the outer ring 4 have a certain thickness, which is the same as the thickness of the circular separator 2, both being 1 mm. To enable the permeation of contaminant in a horizontal direction, the inner ring 3 is made of a permeable membrane material, such as a hollow fiber membrane or an ultrafiltration membrane. To avoid crushing and moving the inner rings 3 during stacking of the plurality of circular separators 2, the outer ring 4 is made of a rigid material to serve as a support. The bottom of the circular separator 2 is fittedly provided with a soil-bearing net 6, which is configured to receive the soil. To avoid the soil loss, the soil-bearing net has a hole size of 6 is 5-15 m and is made of nylon or stainless steel. To avoid the deformation of the soil-bearing net 6 in the vertical direction and render the soil-bearing net 6 a better support effect, a plurality of spokes 5 passing through the center of the soil-bearing net 6 are also fixedly arranged on bottom of the soil-bearing net 6. The plurality of spokes 5 are made of a rigid material to prevent the soil-bearing net 6 from being deformed.

Figure 5:
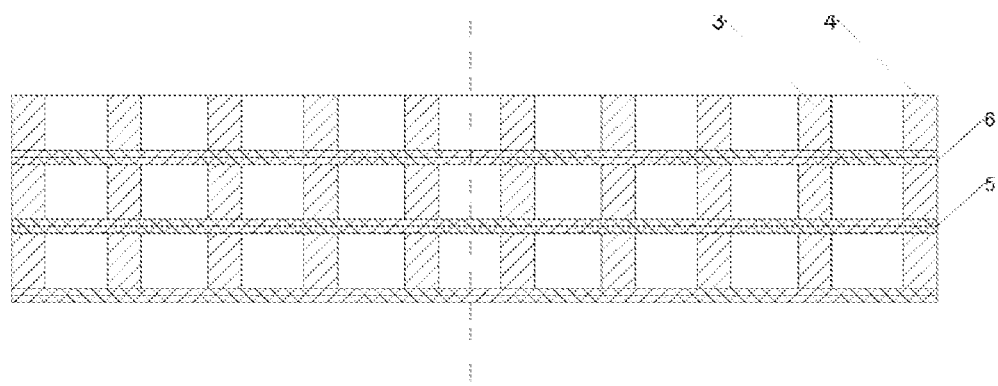
FIG. 5 is a sectional view of multiple circular separators after stacked together according to an embodiment of this disclosure.

As shown in FIG. 5, adjacent three circular separators 2 are stacked. Since the circular separators 2 have a certain thickness, when used, the soil is located between adjacent two circular separators 2 and is borne by the soil-bearing net 6.

This application also provides a soil sampling method by using the aforementioned micro-zone soil sampling apparatus, which includes the following steps.

(S1) A plurality of soil samples from different layers are pre-treated by refining and drying. The plurality of soil samples are spread evenly onto the plurality of circular separators 2, respectively. The plurality of circular separators 2 filled with the layered soil are successively placed in the hollow inner cavity of the uncovered cylinder 1 from a top of the uncovered cylinder, and the plurality of circular separators are respectively fixed to a corresponding height position on the inner wall of the uncovered cylinder, that is, the plurality of circular separators 2 are arranged and stacked according to the height positions of the different soil depths.

(S2) After the filling, according to the type and concentration of contaminants investigated at the contamination site, an exogenous pollutant is added to a center of the uppermost layer of the plurality of circular separators 2. The type of the exogenous pollutant can be flexibly configured as needed. The exogenous pollutant also can be added to an upper surface of the uppermost layer of the plurality of circular separators. The exogenous contaminant is added through single contamination addition, combined contamination addition, low-concentration contamination addition, high-concentration contamination addition, intermittent contamination, or continuous contamination. The single contamination and the combined contamination are performed through steps of: preparation of heavy metals (such as chromium and arsenic) solutions, organic pollutants (such as halogenated hydrocarbons and polychlorinated biphenyls (PCBs)), and composite solutions of heavy metals and organic pollutants (such as a mixture of chromium and PCBs) as exogenous pollutants; and addition of the exogenous pollutants by uniform spraying. The low-concentration contamination and the high-concentration contamination are performed through step of: determination of the concentration level of pollutants by researching existing literature or field surveys of contaminated sites, e.g., 20 mg/kg of exogenous arsenic to the soil is used as a low-concentration contamination addition, and 100 mg/kg of exogenous arsenic to the soil is used as a high-concentration contamination addition; and addition of the exogenous pollutants by uniform spraying. The intermittent contamination refers to that the pollutant is added in a discontinuous manner, e.g., the exogenous pollutant is added every one day for a total of 5 doses. The continuous contamination refers to that the pollutant is added in a continuous manner, e.g., the exogenous pollutant is added by continuous uniform spraying for 48 hours.

After the addition of the exogenous pollutant, simulated rain is sprayed onto the plurality of soil samples, where a rainfall intensity of the simulated rain is determined according to an average rainfall per unit time or by simulating a rainfall intensity of a heavy rain according to a maximum rainfall.

(S3) Then, when collecting the soil samples, the plurality of circular separators 2 are successively removed from the hollow inner cavity of the uncovered cylinder 1 from up to bottom to achieve vertical differentiation of a millimeter-scale micro-zone of a contaminated site. After the plurality of circular separators 2 are removed from the hollow inner cavity of the uncovered cylinder 1, each of the plurality of soil samples is scraped from the hollow spaces of a corresponding circular separator 2 successively, so as to achieve vertical differentiation of the millimeter-scale micro-zone of the contaminated site.

(S4) The plurality of soil samples are analyzed by physicochemical property determination, contaminant concentration monitoring, and microbiological phase analysis.

The embodiments described above are only preferred embodiments of the present disclosure, and are not intended to limit the present disclosure. Though the disclosure has been described in detail above, various changes and modifications can be still made by one of ordinary skill in the art. It should be understood that those changes and modifications made based on the content disclosed herein without paying creative effort shall fall within the scope of the present disclosure defined by the appended claims.

What is claimed is:

1. A micro-zone soil sampling apparatus, comprising:
an uncovered cylinder; and
a plurality of circular separators;
wherein the plurality of circular separators are vertically arranged in a hollow inner cavity of the uncovered cylinder, and are removably connected to an inner wall of the uncovered cylinder; a connection between an outer circumference of each of the plurality of circular separators and an inner wall of the uncovered cylinder is sealed; and adjacent two circular separators are stacked;
each of the plurality of circular separators comprises a plurality of inner rings, an outer ring, and a soil-bearing net; the plurality of inner rings are arranged coaxially; the outer ring is coaxially arranged outside the plurality of inner rings; the plurality of inner rings and the outer ring are arranged evenly spaced apart; each of the plurality of circular separators is divided into a plurality of circular hollow spaces by the plurality of inner rings and the outer ring; the plurality of inner rings and the outer ring both have a certain thickness; the plurality of inner rings are made of a permeable membrane material, and the outer ring is made of a rigid material; the soil-bearing net is fittedly fixed on bottom of each of the plurality of circular separators, and is configured to bear a micro-zone soil sample; and a plurality of spokes passing through a center of the soil-bearing net are fixedly arranged on bottom of the soil-bearing net.

2. The micro-zone soil sampling apparatus of claim 1, wherein each of the plurality of circular separators has a thickness of 1 mm, and comprises at least four inner rings.

3. The micro-zone soil sampling apparatus of claim 1, wherein the soil-bearing net has a hole size of 5-15 m, and is made of nylon or stainless steel; and the plurality of spokes are made of a rigid material.

4. The micro-zone soil sampling apparatus of claim 1, wherein bottom of the uncovered cylinder is evenly provided with a plurality of through holes having a diameter of 1-3 mm.

5. A soil treatment method by using the micro-zone soil sampling apparatus of claim 1, comprising:
(S1) pre-treating a plurality of soil samples from different layers; spreading the plurality of soil samples evenly onto the plurality of circular separators, respectively; and successively placing the plurality of circular separators in the hollow inner cavity of the uncovered cylinder from top of the uncovered cylinder, and fixing the plurality of circular separators on the inner wall of the uncovered cylinder;
(S2) adding an exogenous pollutant to the uppermost layer of the plurality of circular separators; and spraying simulated rain on the plurality of soil samples from the top of the uncovered cylinder;
(S3) successively removing the plurality of circular separators from the hollow inner cavity from top to bottom to achieve vertical differentiation of a millimeter-scale micro-zone of a contaminated site; after the plurality of circular separators are removed from the hollow inner cavity of the uncovered cylinder, scraping each of the plurality of soil samples from the hollow spaces of a corresponding circular separator successively, so as to achieve vertical differentiation of the millimeter-scale micro-zone of the contaminated site; and
(S4) analyzing the plurality of soil samples.

6. The soil sampling method of claim 5, wherein in step (S1), the plurality of soil samples are pre-treated by refining and drying.

7. The soil sampling method of claim 5, wherein in step (S2), the exogenous pollutant is added at a center or an upper surface of the uppermost layer of the plurality of circular separators.

8. The soil sampling method of claim 5, wherein in step (S2), the exogenous pollutant is a single pollutant or a compound pollutant; and the pollutant is added according to different concentrations in an intermittent or continuous manner.

9. The soil sampling method of claim 5, wherein in step (S2), an intensity of the simulated rain is determined according to an average rainfall per unit time or by simulating a rainfall intensity of a heavy rain according to a maximum rainfall.

10. The soil sampling method of claim 5, wherein in step (S4), the plurality of soil samples are analyzed for physicochemical property, pollutant level, and microbial composition.

* * * * *